United States Patent [19]

Lai et al.

[11] 4,207,228

[45] Jun. 10, 1980

[54] UV-LIGHT-STABILIZED COMPOSITIONS CONTAINING SUBSTITUTED 1,5-DIAZACYCLOALKANES, NOVEL COMPOUNDS AND SYNTHESIS THEREOF

[75] Inventors: John T. Lai, Broadview Heights; Pyong N. Son, Akron, both of Ohio

[73] Assignee: The B. F. Goodrich Company, Akron, Ohio

[21] Appl. No.: 835,069

[22] Filed: Sep. 21, 1977

[51] Int. Cl.² ............... C07D 243/12; C07D 245/02; C08K 5/34
[52] U.S. Cl. ............... 260/45.8 N; 260/239 BC; 260/239 BD; 260/239.3 B; 260/239.3 R; 106/176; 252/403
[58] Field of Search ............... 260/239.3 B, 239.3 R, 260/45.8 NH; 106/176; 252/401

[56] References Cited

U.S. PATENT DOCUMENTS

| | | | |
|---|---|---|---|
| 3,769,259 | 10/1973 | Chalmers | 260/45.8 NH |
| 3,962,255 | 6/1976 | Chalmers | 260/239.3 R |
| 3,966,711 | 6/1976 | Rasberger | 260/239.3 R |

FOREIGN PATENT DOCUMENTS 208872  5/1960  Austria ............................. 260/239.3 R

*Primary Examiner*—Henry R. Jiles
*Assistant Examiner*—Robert T. Bond
*Attorney, Agent, or Firm*—J. Hughes Powell, Jr.

[57] ABSTRACT

Novel polysubstituted 1,5-diazacycloalkanes and polysubstituted 2-keto-1,5-diazacycloalkanes are powerful stabilizers for materials subject to ultraviolet (UV) light degradation, particularly for polyolefins. The cyclic compounds of this invention have (a) a fixed three-carbon bridge between the $N^1$ and $N^5$ atoms of the diaza ring, the remaining portion of the ring having a variable length bridge of two or more carbon atoms, (b) an N-adjacent carbon atom of the diaza ring is polysubstituted, that is, has two substituents which may be cyclizable.

Compositions containing (a) the polysubstituted 1,5-diazacycloalkanes and polysubstituted 2-keto-1,5-diazacycloalkanes of this invention, and (b) prior art polysubstituted 1,5-diazacycloalkanes and polysubstituted 2-keto-1,5-diazacycloalkanes, exhibit excellent stability to UV light.

A novel synthesis for preparing polysubstituted 2-keto-1,5-diazacycloalkanes is disclosed.

16 Claims, No Drawings

UV-LIGHT-STABILIZED COMPOSITIONS CONTAINING SUBSTITUTED 1,5-DIAZACYCLOALKANES, NOVEL COMPOUNDS AND SYNTHESIS THEREOF

BACKGROUND OF THE INVENTION

Any material, whether natural or synthetic must exhibit satisfactory resistance to degradation under conditions of use, if products made from the materials are to find a lasting market. A lack of satisfactory resistance to degradation usually manifests itself as a partial or total loss of structural integrity, a darkening or discoloration of the product, a loss of flexibility or resilience, or a combination of the above phenomena. These phenomena are promoted or catalyzed by air (oxygen), heat and light, particularly ultraviolet light.

To protect materials, ingredients which can be collectively called stabilizers are admixed with the materials to prevent or inhibit degradation. These stabilizers work in diverse and complex ways, such that a compound which stabilizes against heat and oxygen degradation in a material may not stabilize against light degradation in the same material, or vice versa. Furthermore, a compound which acts as a stabilizer against oxygen degradation in one type of material may be relatively inactive in another type of material. Thus compounds which are stabilizers are further classed as antioxidants, antiozonants, heat stabilizers and ultraviolet (UV) light stabilizers, depending upon what type of activity and stabilization they demonstrate. In many cases, to obtain optimum protection, a mixture of compounds, each specifically selected to afford maximum protection against a certain type of degradation, is often used. In some instances stabilizers are deliberately chosen to counter the adverse effects of a plasticizer which, though highly effective as a plasticizer, tends to accelerate UV degradation. In other words, the plasticized material is more suceptible to degradation than if no plasticizer was added. As a general empirical rule, it is found that plasticizers are marginally effective as stabilizers, and stabilizers are marginally effective as plasticizers, it being more likely that a compound with desirable stabilizer properties has undesirable plasticizer properties, and vice versa.

The present invention is directed to (a) novel UV light stabilizers classed as hindered amines- more specifically classed as hindered cyclic diazaalkanes and keto-diazaalkanes, (b) novel compositions in which the cyclic diazacycloalkanes and keto-diazacycloalkanes are incorporated and, (c) a novel synthesis for the cyclic keto-diazacycloalkanes. The basic structure of these novel compounds is a polysubstituted 1,5-diazacycloalkane having (a) fixed three-carbon bridge between the two N atoms (the $N^1$ and $N^5$ atoms) of the diaza ring, the remaining portion of the ring having a variable length bridge of two or more carbon atoms, and (b) at least the $N^5$-adjacent carbon atom of the fixed three-carbon bridge has two substituents (hence "polysubstituted"), which may be cyclizable, that is, form a cyclic substituent. When the compound is a polysubstituted 2-keto-1,5-diazacycloalkane, it additionally includes an $N^1$-adjacent carbonyl in the fixed three-carbon bridge of the 1,5-diaza ring. These compounds which may be monocyclic, or with cyclizable substituents, may be bicyclic or tricyclic, are particularly useful as UV light stabilizers in substantially colorless organic substrates. They may also form dimers and biscompounds. The diaza ring of the basic structure may have from 6 to 9 ring members, more preferably from 6 to 8 ring members, and most preferably from 6 to 7 ring members.

It is known that 2-keto-4,4,6,6-tetramethyl-1,5-diazacycloheptane may be prepared by a Schmidt's rearrangement of a six-membered ring with sodium azide (see German Pat. No. 2,428,877) but there is no known manner of similarly arriving at an eight membered, 1,5-diaza ring with an $N^1$-adjacent carbonyl. Moreover, though the foregoing 2-keto-diazacycloheptane, identified as 2,2,7,7-tetramethyl-5-oxo-1,4-diazacyclpheptan in the reference, can be synthesized as described, other polysubstituted compounds named cannot be so synthesized. More specifically the 2-keto-1,5-diazapolycycloalkanes named therein cannot be synthesized as described.

It is known that 1,5-benzodiazepin-2-spirocycloalkanes may be made in a one-step condensation from o-phenylenediamine and cyclic ketones such as cyclohexanone in cold ethanol in the presence of boron trifluoride-ether comples. ("Synthesis of Heterocyclic Compounds. Part XXIX. Substituted 2,3-dihydro-1H-1,5-benzodiazepines" by Herbert, John A. A. and Suschitzky, Hans, J. C. S. Perkin I, 1974,2657.) However 1,2-diamincyclohexane does not react under similar conditions.

Further, it is known that $\alpha,\beta$-unsaturated ketones may be added slowly to a methanol solution of aliphatic 1,2-diamine at about 30° C., and the mixture hydrogenated over an Adams catalyst to give 7-alkyl-1,5-diazacycloheptanes also identified as 2-alkyl-1,4-diazacycloheptanes (Bonvincini A and Cantatore G., Chem, Ind. 54, 980 (1972); New Methods in Synthetic Organic Chemistry Selected from the Current Chemical Literature, August 1974). O-phenylenediamine does not react similarly under similar conditions.

In another example, though it is known that 1,2-diaminocyclohexane will react with acetone cyanohydrin to form cis-3,3-dimethyl-decahydroquinoxalin-2-one (Bindler, U.S. Pat. No. 2,920,077), no analogous reaction occurs with o-penylenediamine. Thus, it is evident that o-phenylenediamine and 1,2-diaminocyclohexane are essentially different types of amines particularly with respect to the reactions they enter.

It is also known that cyclo condensation of $\beta,\beta$-dimethylacrylic acid with o-phenylenediamine and its derivatives yields 2-keto-1,5-benzodiazepines (Khakimova, N. K. et al, Inst. Khim.Rast. Veshechestv, Tashkent, USSR; USB. Khim. Zh. 1975, 19(2), P 53–55). The $N^5$-adjacent carbon of the fixed three-carbon ring is disubstituted, and the benzene ring may have a hydrogen, chlorine or methyl substituent. The reference compounds have no utility as UV light stabilizers. It has now been found that, under strenuous hydrogenating conditions of above about 200° C. and 2000 psi, the 2-keto-1,5-benzodiazepines of the Russian reference may be hydrogenated in alcohol to the 2-keto-decahydro-benzodiazepine without rupturing the ring structure, though we are aware of no teaching that would indicate a seven-membered 1,5-diaza ring could withstand such strenuous conditions, or that such hydrogenation could be accomplished.

In fact, known quinioline derivatives such as 1,2,3,4-tetrahydro-3,3,6 (or 7)-trimethylquinoline is not hydrogenated under similar conditions, namely 200° C. and 2000 psi in the presence of Raney's nickel, but decomposes.

Except for the 2-keto-1,5-diazacycloheptane compounds disclosed in the aforementioned German reference there is no teaching to suggest that polysubstituted 1,5-diazacycloalkanes and polycyclic polysubstituted 2-keto-1,5-diazacycloalkanes would be effective UV-light stabilizers.

SUMMARY OF THE INVENTION

UV-light-stable compositions have been discovered in which an organic substrate consisting essentially of a polyhydrocarbon, polyester, polyester resin, polyamide, vinyl polymer, cellulose ether or cellulose ester, has uniformly dispersed therein, an effective amount of a polysubstituted 1,5-diazacycloalkane or a 1,5-diazacycloalkan-2-one UV-light absorbing compound sufficient to make the substrate UV light stable.

More specifically, novel UV-light-stable compositions have been discovered in which the stabilizers are polysubstituted 1,5-diazacycloalkanes or polysubstituted 2-keto-1,5-diazacycloalkanes having (a) a fixed three-carbon bridge between the N atoms of the diaza ring, the remaining portion of the ring having a bridge of variable length comprising from two to about three carbon atoms, and (b) the $N^5$-adjacent carbon atom of the fixed three-carbon bridge has two substituents which may be cyclizable. The polysubstituted 2-keto-1,5-diazacycloalkanes also include an $N^1$-adjacent carbonyl in the fixed three-carbon bridge.

Though desirable stabilization of an organic substrate may be obtained with two substituents on the $N^5$-adjacent C atom of the fixed three-carbon bridge of a diazacycloalkane or a 2-keto-diazacycloalkane, it has been discovered that additional substituents, including at least one particularly on the $N^5$-adjacent C atom of the variable length bridge, provides superior UV-light-stability.

It has further been found that, in addition to UV-light compositions which include aforementioned polysubstituted 1,5-diazamonocycloalkanes and 2-keto-1,5-diazamonocycloalkanes, excellent UV light stability may also be obtained with polysubstituted 1,5-diazapolycycloalkanes and 2-keto-1,5-diazapolycycloalkanes, all of which are preferably used in the range from about 0.1–1.0 part stabilizer per 100 parts substrate.

It is therefore an object of this invention to provide a UV-light-stable composition in which is uniformly dispersed a 1,5-diazapolycycloalkane, or 2-keto-1,5-diazapolycycloalkane having two substituents which may be cyclizable, on the $N^5$-adjacent C atom in the fixed bridge; and preferably, having a total of at least three substituents on the symmetrical $N^5$-adjacent C atoms, some of which substituents together with the C atoms to which they are bound, may be cyclizable.

In addition to the foregoing novel compositions, novel cyclic hindered amine compounds have been discovered which imbue an organic substrate with exceptional UV light stability, and these cyclic hindered amines are 2-keto-1,5-diazacycloalkanes having (a) a fixed three-carbon bridge between the N atoms of the diaza ring, the remaining portion of the ring having a bridge of variable length comprising from two to about three carbon atoms, (b) an $N^1$-adjacent carbonyl in the fixed bridge and (c) the $N^5$-adjacent carbon of the fixed bridge has two substituents, which may be cyclizable, and the $N^5$-adjacent carbon of the variable length bridge has at least one substituent.

More specifically, novel substituted 2-keto,1,5-diazacycloalkanes have been discovered in which (a) the symmetrical $N^5$-adjacent C atoms have a total of at least three acyclic substituents, or, (b) only the $N^5$-adjacent C atom of the fixed bridge has a cyclic substituent, or (c) each $N^5$-adjacent C atom has the some or different cyclic substituents.

It has also been discovered that diaminocycloalkanes may be reacted with $\beta,\beta$-dialkyl substituted $\alpha,\beta$-unsaturated acids or esters, acylhalides or amides to yield any one of various ketones such as a bicyclo-1,5-diazaalkan-2-one with a disubstituted $N^5$-adjacent carbon in the fixed three-carbon bridge of the diaza ring. The bicyclo-1,5-diazaalkan-2-one with a disubstituted $N^5$-adjacent carbon in the fixed three-carbon bridge of the diaza ring. The bicyclo-1,5-diazaalkan-2-one may subsequently be hydrogenated over an Adam's catalyst or Raney's Nichel to a bicyclo-1,5-diazaalkane. In an analogous manner, polycyclo-1,5-diazaalkan-2-ones may be formed.

It is therefore a general object of this invention to provide novel polysubstituted 2-keto-1,5-diazacycloalkanes and 1,5-diazacycloalkanes in which one or more diaza ring carbon atoms are disubstituted with alkyl substituents, or substituents, which together with the C atom or atoms to which they are bound, are cyclizable; or in which only the $N^5$-adjacent C atom of the fixed bridge has a cyclic substituent; or in which each $N^5$-adjacent atom has the same or different substituents whether cyclic or acyclic; to provide a novel method for the synthesis of polysubstituted 2-keto-1,5-diazacycloalkanes and 1,5-diazacycloalkanes; and, to provide organic compositions in which a minor amount, generally less than 1 percent by weight, of a polysubstituted 2-keto-1,5-diazacycloalkane or 1,5-diazacycloalkane provides remarkable UV light stability even compared to known highly regarded UV stabilizers.

DETAILED DESCRIPTION OF PREFERRED EMBODIMENTS

Polysubstituted (hereinafter referred to as "substituted" for brevity) 2-keto-1,5-diazacycloalkanes and/or 1,5-diazacycloalkanes, in which at least the $N^5$-adjacent C atom of the fixed three-carbon bridge has two substituents which may be cyclizable, when incorporated into UV-light-degradable organic materials, exhibit a surprisingly powerful stabilizing effect. The stabilizers are used in the range from about 0.01 to about 1.0 percent, per 100 parts of organic substrate subject ot UV light. Compositions which include these stabilizers are conveniently and economically prepared. The UV stabilizing effect of these compounds, substantially disappears when each carbon of the diaza ring is unsubstituted, and the stabilizing effect is too slight to be practical even when each symmetrical $N^5$-adjacent C atom is monosubstituted. In fact, when the 2-keto-1,5-diazacycloalkane is a seven-membered ring, this lack of a practical level of UV stability is manifest when the $N^5$-adjacent C atom of the fixed, three-carbon bridge is not disubstituted, or does not have a cyclic substituent. It is therefore essential for good stability, that the $N^5$-adjacent C atom of the fixed three-carbon bridge be disubstituted, or have a cyclic substituent, irrespective of the number of members in the 2-keto diaza ring. It is preferred, for superior UV stabilizing performance, that some substituents on the 2-keto diaza ring be cyclizable so as to provide a diazapolycycloalkane, such as a diazabicycloalkane or diazatricycloalkane. It is more preferred that the stabilizer compounds be bicycloalkanes having seven or eight membered 1,5-diaza rings, and that the $N^5$-adjacent carbon of the fixed three-carbon bridge be disubstituted with acyclic substituents. The variable length bridge has two or more C atoms and may have substituents on one or more of the C atoms of the variable length bridge, and these substituents may be cyclizable.

Compositions of this invention contain UV light stabilizers selected from the group consisting of 1,5-diazacycloalkanes having the structural formula

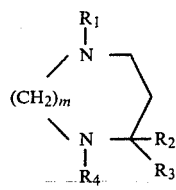

and 2-keto-1,5-diazacycloalkanes having the structural formula

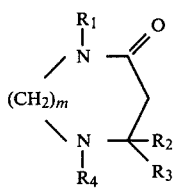

wherein, m represents an integer in the range from 2 to 7, being the number of methylene groups forming a bridge of variable length, and some of which groups (a) together with the carbons to which they are bound, may form a cyclopentyl, cyclohexyl or cycloheptyl endo ring, or (b) be substituted; when m is 2 then (I) represents a substituted 1,5-diazacycloheptane, and when m is 6 and cyclized then (I) typically represents s substituted decahydrobenzodiazepine.

$R_1$ and $R_4$ independently represent hydrogen, alkyl having from 1 to about 24 carbon atoms, hydroxyalkyl having from 1 to about 12 carbon atoms, haloalkyl having from 1 to about 12 carbon atoms, cyanoalkyl having from 2 to about 12 carbon atoms, aminoalkyl or iminoalkyl having from 1 to about 12 carbon atoms, ether groups having from 3 to about 18 carbon atoms, nitrosyl, hydroxyalkyl ether or cyanoalkyl ether groups having from 4 to about 18 carbon atoms, alkenyl and aralkyl having from 7 to about 14 carbon atoms, alkylene having from 1 to about 7 carbon atoms and optionally containing a phosphite, ester or hindered phenol group; $R_4$ may be oxygen, and, $R_2$ and $R_3$ on the $N^5$-adjacent carbon of the fixed three-carbon bridge independently each represent alkyl having from 1 to about 12 carbon atoms, haloalkyl having from 1 to about 12 carbon atoms, cycloalkyl having from 2 to about 12 carbon atoms, aminoalkyl or iminoalkyl having from 2 to about 12 carbon atoms, cycloalkyl having from 5 to about 14 carbon atoms, hydroxy-cycloalkyl having from 5 to about 14 carbon atoms, alkenyl and aralkyl having from 7 to about 14 carbon atoms, alkylene having from 1 to about 7 carbon atoms and optionally containing a phosphite, ester or hindered phenol group, and which in combination, one with another, represent cycloalkyl having from 5 to about 14 carbon atoms at least four of which are cyclized and optionally containing a keto, ester, amide, ether, thio or hydroxy group.

When the compositions of this invention include a stabilizer compound having a substituted alkylene group in the variable length bridge of the above-identified structural formula I, the compound may be represented by a structural formula selected from

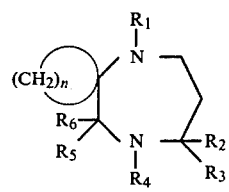

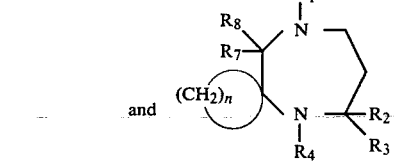

When the compositions of this invention include a stabilizer compound having a substituted alkylene group in the variable length bridge of the above identified structural formula (II) the compound may be represented by a structural formula selected from

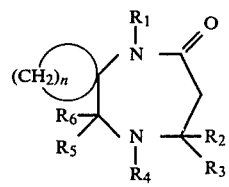

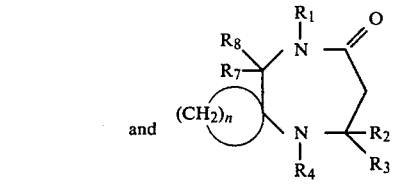

wherein n represents an integer in the range from 0 to about 6; so when n is 0 then (III) and (IV) represent substituted 1,5-diazacycloheptane, and when n is 4 with the variable length bridge cyclized, then (III) and (IV) represent decahydrobenzodiazepine; and, $R_5, R_6, R_7, R_8$ in the variable length bridge have the same connotation as $R_2$ and $R_3$ in (I) hereinabove, and additionally may be H, except that $R_5$ and $R_6$ are different if either is H; $R_2, R_3$ may be cyclizable, as may be $R_5, R_6$ and $R_7, R_8$; and, if cyclized, the cyclic substituents may be the same or different.

Illustrative of the type of substituents that are effectual in the above-identified 1,5-diazacycloalkanes and 2-keto-1,5-diazacycloalkanes are:

where $R_1$ and/or $R_4$ is alkyl, examples are methyl, ethyl, n-propyl, n-butyl, t-butyl, n-hexyl, n-octyl, 2-ethylhexyl, n-decyl, n-tetradecyl, n-octyldecyl, and the like;

where $R_1$ and/or $R_4$ is hydroxyalkyl, examples are 2-hydroxyethyl, 2-hydroxpropyl, 3-hydroxypropyl, 2-hydroxybutyl, 6-hydroxyhexyl, 8-hydroxyoctyl, and the like;

where $R_1$ and/or $R_4$ is haloalkyl, examples are 2-chloroethyl, 2-bromoethyl, 2-flouroethyl, 2-chlorobutyl, 4-chlorobutyl, 2-chlorethylhexyl, and the like;

where $R_1$ and/or $R_4$ is cyanoalkyl, examples are 2-cyanoethyl, 3-cyanopropyl, 4-cyanobutyl, 8-cyanoctyl, and the like;

where $R_1$ and/or $R_4$ is aminoalkyl or iminoalkyl, examples are 2-aminoethyl, 3-aminopropyl, 4-aminobutyl, 6-aminohexyl, 2-methyl, 2-aminoethyl, and the like;

where $R_1$ and/or $R_4$ is ether, examples are methoxyethyl, ethoxyethyl, ethoxypropyl, octyloxyethyl, phenoxyethyl, p-methylphenoxypropyl, and the like; when R is hydroxyalkylether or cyanoalkyl ether, examples are 2-hydroxyethyloxaethyl, p-(2-hydroxypropyl), phenyloxapropyl, 4-hydroxybutyloxahexyl, 2-cyanoethyloxaethyl, 2-hydroxyethyl-di(oxaethyl), and the like;

for $R_2,R_3,R_5,R_6,R_7$ and $R_8$, examples are methyl, ethyl, propyl, n-butyl, isobutyl, n-hexyl, 2-ethylheptyl, n-decyl, and where the substituents are cyclizable, cyclopentyl, methylcyclopentyl, cyclohexyl, methylcyclohexyl, dimethyl cycloheptyl, piperidyl, 2-2',6-6'-tetramethyl piperidyl, and the like.

Novel compounds of this invention are those represented by formulae (II, (V), and (VI) wherein: n represents an integer in the range from 1 to about 6 so as to present a carbon bridge of variable length having at least 2 carbon atoms bridging the N atoms, and two of the carbon atoms together with substituents thereon, may form a cyclopentyl, cyclohexyl or cycloheptyl ring;

$R_1$ and $R_4$ have the same connotation as in (I) and (II) hereinabove;

$R_2, R_3, R_5, R_6, R_7$ and $R_8$ each independently represents an acyclic substituent provided that when n=0 the diaza ring is, at least seven membered;

$R_2,R_3$ may be cyclizable, as may be $R_5,R_6$, and $R_7,R_8$, and the cyclic substituents $R_2,R_3$ and $R_5,R_6$ are the same or different;

$R_2,R_3$ may be cyclizable and $R_5,R_6,R_7,R_8$ may each independently represent an acyclic substituent.

Examples of specific novel substituted mono-keto-diazacycloalkan-2-ones wherein the $N^5$-adjacent C atom of the fixed three-carbon bridge has two substituents which may be cyclizable, are:

(a) diazamonocycloalkan-2-ones having a total of more than four substituents on the diaza ring, for example, 4,4,6,6,7-pentaalkyl-1,5-diazepin-2-one;

(b) trans-1,5-diazabicycloalkan-2-ones for example, trans-4,4-dialkyl-decahydrobenzodiazepin-2-one; and, (c) mono keto-1,5-diazatricycloalkan-2-ones, for example, 3,3-($\beta,\beta'$-di-tert-butyl amine) decahydrobenzodiazepin-2-one.

The more preferred substituent 2-keto-1,5-diazacycloalkane compounds are those wherein $R_1$ and/or $R_4$ is alkyl having from 4 to 18 carbon atoms, benzyl, cyclohexylmethyl, hydroxyalkyl having from 1 to about 6 carbon atoms, hydroxyalkyl ether having from 4 to about 12 carbon atoms, cyanoalkyl having from 2 to about 6 carbon atoms, and aminoalkyl having from 1 to about 6 carbon atoms; $R_2,R_3,R_5,R_6,R_7$ and $R_8$ are alkyl having from 1 to about 12 carbon atoms, or polymethylene having from 5 to 6 carbon atoms which are cyclizable; only $R_2,R_3$ may be cyclized, or $R_2,R_3$ and $R_5, R_6$ may be cyclized; and if $R_2,R_3$, and $R_5,R_6$ are each cyclized, the cyclic substituents may be the same or different; and n is a numeral in the range from 4 to about 6 when the methylene groups are cyclized. The $C^3$ carbon adjacent the carbonyl in the fixed bridge may also be substituted, but the effect of such substitution on the UV light stability of the compounds is insubstantial.

Examples of the aforespecified more preferred substituted mono-keto-1,5-diazaalkan-2-ones are:

(a) 1-(alkyl)-4,4,7,7-tetraalkyl-hexahydro-1,5-diazepin-2-ones having the structure

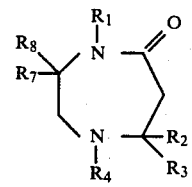

wherein $R_1$ or $R_4$ or each is alkyl having from 1 to about 20 carbon atoms, and $R_2,R_3,R_7$ and $R_8$ are each lower alkyl having from 1 to about 5 carbon atoms; for example, 1-(n-octyl)-4,4,7,7-tetramethyl-hexahydro-1,5-diazepin-2-one;

(b) 1(or 4)-(alkyl)-4,4,6,6-tetraalkyl-hexahydro-1,5-diazepin-2-ones having the structure

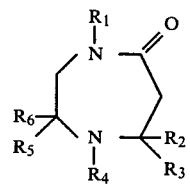

wherein $R_1,R_2,R_3$, and $R_4$ have the same connotation as in (a) above, and $R_5$ and $R_6$ are each lower alkyl having from 1 to about 5 carbon atoms; for example 1-(n-octyl)-5-(n-butyl)-4,4,6,6-tetramethyl-1,5-diazepin-2-one;

(c) 1 (or 5)-(alkyl)-4,4,6,6-tetraalkyl-hexahydro-1,5-diazacyclooctan-2-ones having the structure

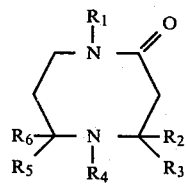

wherein $R_1$ to $R_6$ have the same connotation as in (b) immediately above; for example 1-(n-octyl)-5(n-butyl)-4,4,6,6-tetramethyl-1,5-diazacyclooctan-2-one;

(d) 1(or 5)-(alkyl)-4,4,6,6,8-pentaalkyl-1,5-diazacyclooctan-2-one having the structure

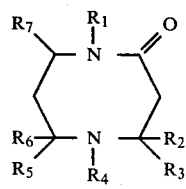

wherein $R_1$ to $R_6$ have the same connotation as in (b) above, and $R_7$ is lower alkyl having from 1 to about 5 carbon atoms; for example 1-(n-butyl)-4,4,6,6,7-pentamethyl-1,5-diazacyclooctan-2-one;

(e) cis and trans isomers of 1 (or 5) (alkyl)-4,4-dialkyl-decahydro-1,5-benzodiazepin-2-one having the structure

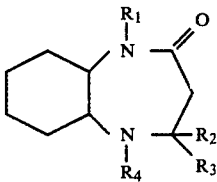

wherein $R_1$ to $R_4$ have the same connotation as in (a) hereinabove; for example cis-1-(n-butyl)-decahydro-4,4-dimethyl-1,5-benzodiazepin-2-one;

(f) 1 (or 5) (alkyl)-4,4-dialkyl-hexahydro-1,5-benzodiazacyclooctan-2-ones having the structure

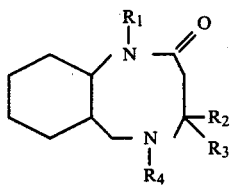

wherein $R_1$ to $R_4$ have the same connotation as in (a) hereinabove; for example, $N^1$-butyl-$N^5$-($\beta$-hydroxyethyl)-4,4-dimethyldecahydro-1,5-benzodiazacyclooctan-2-one.

Most preferred substituted mono-keto-1,5-diazacycloalkan-2-ones are:

cis-4,4-dimethyl-decahydro-1,5-benzodiazepin-2-one;
trans-4,4-dimethyl-decahydro-1,5-benzodiazepin-2-one;
cis-$N^1$-benzyl-4,4-dimethyl-decahydro-1,5-benzodiazepin-2-one;
cis-$N^1$-dodecyl-4,4-dimethyl-decahydro-1,5-benzodiazepin-2-one;
cis-$N^5$-$\beta$-hydroxyethyl-4,4-dimethyl-decahydro-1,5-benzodiazepin-2-one;
$N^1$-butyl-$N^5$-($\beta$-hydroxyethyl)-4,4,6,6,8-pentamethyl-1,5-diazacyclooctan-2-one;
$N^1$-dodecyl-4,4,6,6,8-pentamethyl-1,5-diazacyclooctan-2-one;
$N^1$-octyl-4,4,6,6,9,9-hexamethyl-1,5-diazacyclononan-2-one;
$N^1,N^5$-bis ($\beta$-hydroxyethyl)-4,4,6,6,9,9-hexamethyl-1,5-diazacyclononan-2-one;
bis-[2-(4,4,6,6,9,9-hexamethyl-1,5-diaza-2-cyclononanone-1-yl)ethyl]sebacate;
$N^1$-benzyl-4,4-pentamethylene-trans-decahydro-1,5-benzodiazepin-2-one;
1,6-benzyl-bis-($N^1$-trans-4,4-dimethyl-decahydro-1,5-benzodiazepin-2-one;
4,4-dimethyl-5-hydroxyethyl-decahydro-1,5-benzodiazepin-2-one;
4,4-dimethyl-5-ethyl-decahydro-1,5-benzodiazepin-2-one;
4,4-dimethyl-5-dodecyl-decahydro-1,5-benzodiazepin-2-one;
4,4-dimethyl-5-propyl-decahydro-1,5-benzodiazepin-2-one;
4,4-dimethyl-5-butyl-decahydro-1,5-benzodiazepin-2-one.

Examples of the aforespecified more preferred substituted 1,5-diazacycloalkanes are:

(a) 1 (or 5)-(alkyl)-4,4,7,7-tetraalkyl-1,5-diazepines having the structure

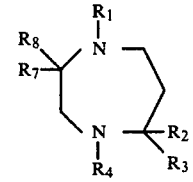

wherein $R_1$ or $R_4$, or each is alkyl having from 1 to about 20 carbon atoms, and $R_2,R_3,R_7$ and $R_8$ are each lower alkyl having from 1 to about 5 carbon atoms; for example, 1-(n-octyl)-4,4,7,7-tetramethyl-hexahydro-1,5-diazepine;

(b) 1 (or 5)-(alkyl)-4,4,6,6-tetraalkyl-hexahydro-1,5-diazepines having the structure

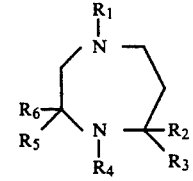

wherein $R_1$ to $R_4$ have the same connotation as in (a) immediately hereinabove, and $R_5$ and $R_6$ are each lower alkyl having from 1 to about 20 carbon atoms; for example, 1-(n-octyl)-5-(n-butyl)-4,4,6,6-tetramethyl-hexahydro-1,5-diazepine;

(c) 1(or 5)-(alkyl)-4,4,6,6,7-pentaalkyl-hexahydro-1,5-diazepines having the structure

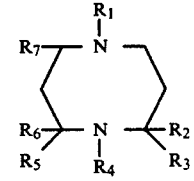

wherein $R_1$ to $R_7$ have the same connotation as in (a) and (b) immediately hereinabove; for example, 1-(n-butyl)-4,4,6,6,7-pentamethyl-hexahydro-1,5-diazepine;

(d) cis and trans isomers of 1 (or 5)-(alkyl)-4,4-dialkyl-decahydro-1,5-benzodiazepines having the structure

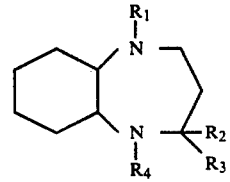

wherein $R_1$ to $R_4$ have the same connotation as in (a) hereinabove; for example, cis-1-(n-butyl)decahydro-4,4-dimethyl-1,5-benzodiazepine.

Most preferred substituted 1,5-diazacycloalkanes are cis-and trans-2,2,4-trimethyl-decahydro-1,5-benzodiazepine;
cis-and trans-$N^1,N^5$-bis-$\beta$-hydroxyethyl-2,2,4-trimethyl-decahydro-1,5-benzodiazepine;
1,6-bis (4,4,6,6,8-pentamethyl-1,5-diaza-2-cyclooctanone-1-yl)hexane;
2,2,4,6-tetramethyl-1,4-diazacycloheptane;
1 or 4-($\beta$-hydroxyethyl)-2,2,4,6-tetramethyl-1,4-diazacycloheptane;
$N^1$-dodecyl-2,4,4,6,6,8-hexamethyl-1,5-diazacyclooctane;
1,6-bis (2,4,4,6,6-pentamethyl-1,5-diazacyclo-1-octyl) hexane;

As will be evident, compositions of this invention include 1,5-diazacycloalkane compounds in which the diaza ring has a fixed three-carbon bridge between the two N atoms of the diaza ring, the remaining portion of the ring having a bridge of variable length having two or more carbon atoms. These compositions also include 2-keto-1,5-diazacycloalkane compounds having an $N^1$-adjacent carbonyl and two substituents, which may be cyclizable, on the $N^5$-adjacent carbon in the fixed three-carbon bridge. In addition one or more C atoms of the variable bridge may be substituted with one or more substituents. When the substituents on the variable portion of the diaza ring are cyclizable, for example forming cyclohexyl, cis and trans isomers may be formed. Dimers and bis compounds of polysubstituted 1,5-diazacycloalkanes and polysubstituted 2-keto-1,5-diazacycloalkanes can also be prepared as described hereinafter, and used as effective UV stabilizers.

Compositions of this invention are organic substrates which have been stabilized to combat the deleterious effect of thermal, oxidative or actinic light such as are usually evidenced by discoloration and/or embrittlement. These substrates can be low or high molecular weight materials, and particularly includes homopolymers, copolymers and mixtures thereof. Examples of substrates that can be stabilized against degradation due to UV light are oils; monomers, particularly $\alpha$-$\beta$-olefinically unsaturated monomer such as acrylates, dienes, vinyl nitriles, and the like; and other lower molecular weight materials such as alcohols, aldehydes, and the like. Examples of known substrates which can be stabilized with polysubstituted 2-keto diazacycloalkanes are natural rubber, synthetic rubbers such as cis-polyisoprene, styrenebutadiene rubber, diene-nitrile rubbers, polyepihalohydrin polymers, and the like, polyurethanes, PVC resins, ABS resins, polystyrene, polyacrylonitrile, polymethacrylates, polycarbonates, varnish, phenol-formaldehyde resins, polyepoxides, polyesters, and polyolefin homo and copolymers such as polyethylene, polypropylene, ethylene-propylene polymers, ethylene-propylenediene polymers, ethylenevinyl acetate polymers, and the like. The substituted 2-keto diazacycloalkanes can also be used to stabilize mixtures and blends of polymeric materials such as ABS resin blends, PVC and polymethacrylate blends, and blends of polyolefin homopolymers and copolymers such as blends of polypropylene in epdm polymers.

The substituted 1,5-diazacycloalkanes and 2-keto-1,5-diazacycloalkanes are particularly useful as UV stabilizers for normally solid polymers such as the poly-$\alpha$-monoolefin homopolymers of $\alpha$-olefins having up to 3 carbon atoms, e.g. ethylenepropylene and their copolymers; vinyl resins formed from the polymerization of vinyl halides or from copolymerization of vinyl helides with unsaturated polymerizable compounds, for example vinyl esters, $\alpha,\beta$-unsaturated acids, $\alpha,\beta$-unsaturated esters and unsaturated hydrocarbons; polyurethanes such as are prepared from polyols and an organic polyisocyanate; polyamides such as polymethyleneterephthalates; polycarbonates such as those prepared from bisphenol-A and phosgene; polyacetals; polyethylene oxide; polyacrylics such as polyacrylonitrile; polyphenyleneoxides such as those prepared from 2,6-dimethylphenol and the like. The $\alpha$-monoolefin monomers used to prepare the latter polymers include ethylene, propylene, isobutylene, 1-butene, 1-pentene, 1-hexene, 4-methyl-1-pentene, and the like. Excellent results have been obtained using compounds of this invention, as well as known substituted 1,5-diazacycloalkanes and 2-keto-1,5-diazacycloalkanes to stabilize polypropylene against UV degradation.

The stabilized compositions of this invention are especially useful in those instances where the plastic article made from the stabilized composition is to be used outdoors, or indoors under intense actinic light.

Many known compounding ingredients may be used along with the substituted 1,5-diazacycloalkanes and 2-keto-1,5-diazacycloalkanes in the compositions. Such ingredients include metal oxides such as zinc, calcium and magnesium oxide, fatty acids such as stearic and lauric acid, and salts thereof such as cadmium, zinc and sodium stearate and lead oleate; fillers such as calcium and magnesium carbonate, calcium and barium sulfates, aluminum silicates, asbestos, and the like; plasticizers and extenders such as dialkyl and diaryl organic acids like diisobutyl, diisooctyl, diisodecyl, and dibenzyl oleates, stearated, sebacates, azelates, phthalates, and the like; ASTM type 2 petroleum oils, paraffinic oils, castor oil, tall oil, glycerin, and the like; antioxidants such as 2,6-di-t-butyl paracresol, 2,2'-methylenebis-(4-ethyl-6-t-butylphenol), 2,2'-thiobis-(4-methyl-6-t-butyl-phenol), 2,2' methylenebis-6-t-butyl-4-ethyl phenol, 4,4'-butylene-bis-(6-t-butyl-m-cresol), 2-(4-hydroxy-3,5-di-t-butylanilino)-4,6-bis-(octylthio)-1,3,5-triazine, hexahydro-1,3,5-tris-$\beta$-(3,5-di-t-butyl-4-hydroxyphenyl)propionyl-s-triazine, tris-(3,5-di-t-butyl-4-hydroxybenzyl)isocyanurate, tetrakismethylene-3(3',5'-di-t-butyl-4'-hydroxyphenyl)propionate methane, distearyl thiodipropionate, dilauryl thiodipropionate, tri(nonylphenyl)-phosphite, tin thioglycolate, and the like; and the other ingredients such as pigments, tackifiers, flame retardants, fungicides, and the like.

Compounding ingredients of particular interest to be used in the compositions of the invention are the antioxidant stabilizers. As the 2-keto-diazaalkane compounds of the invention are UV stabilizers, it is beneficial to add antioxidants to the compositions of the invention to achieve both UV light and oxygen stability of the compositions. The antioxidants are used in the range from about 0.1 part to about 10 parts by weight, preferably from about 0.2 part to about 5 parts by weight per 100 parts by weight of the material. Of the types of antioxidants to be used, are phosphate, sulfide and phenolic antioxidants, the last being preferred.

Examples of phenolic antioxidants are 2,6-di-t-butylphenol; 2-methyl-4,6-dinonyl phenol; 2,6-di-t-butyl-p-cresol; 2,2'-methylene-bis-(4-methyl-6-t-butyl phenol);

1,1'-methylene-bis-(2-naphthol); 4,4'-methylene-bis-(2,6-di-t-butyl phenol); 4,4'-thio-bis(6-t-butyl-m-cresol); and the like. Although any phenolic antioxidant used in combination with the substituted 2-keto diazacycloalkanes would improve the heat and oxygen stability of the compositions the more preferred phenolic antioxidants are those having alkylhydroxyphenyl substituents on an ester or a heterocyclic nucleus.

Examples of phenolic antioxidants having alkylhydroxyphenyl substituents on an ester nucleus are compounds disclosed in U.S. Pat. No. 3,330,859 and disclosed in U.S. Pat. No. 3,627,725 and exemplified by di-lauryl α,α'-bis(3,5-di-t-butyl-4-hydroxybenzyl)malonate; compounds exemplified by tetrakis (methylene-3-(3',5'-di-t-butyl-4'-hydroxyphenyl)propionate)methane; and the like.

Examples of phenolic antioxidant compounds having alkyhydroxyphenyl substituents on a heterocyclic nucleus are compounds where the heterocyclic nucleus is a triazine nucleus such as compounds disclosed in British Pat. No. 977,589 and exemplified by 2,4,6-tris(4-hydroxy3,5-di-t-butyl benxylthio)-1,3,5-triazine; compounds disclosed in U.S. Pat. No. 3,706,740 and exemplified by 2,3,6-tris(3',5'-di-t-butyl-4'-hydroxybenzyl)-1,3,5-triazine; disclosed in U.S. Pat. No. 3,567,724 and exemplified by hexahydro-1,3,5-tris-3-(3,5-di-t-butyl-4-hydroxyphenyl)propionyl-s-triazine; disclosed in U.S. Pat. No. 3,694,440 and exemplified by 1,3,5-tris(4'-hydroxy-3',5'-di-t-butylphenylpropionyloxyethylthio-propionyl)hexahydro-1,3,5-triazine; and the like.

Examples of phenolic antioxidant compounds having alkylhydroxyphenyl substituents on a isocyanurate nucleus are compounds of the formula disclosed in U.S. Pat. No. 3,531,483 and exemplified by tris-(3,5-di-t-butyl-4-hydroxybenzyl)isocyanurate; disclosed in U.S. Pat. No. 3,678,047 and exemplified by 2,2',2''-tris(3-(3,5-di-t-butyl-4-hydroxyphenyl)propionyloxy)ethyl isocyanurate; and the like.

Still other hindered phenols useful as thermal antioxidants are disclosed in U.S. Pat. No. 3,920,659, and in copending U.S. patent applications Ser. No. 697,345 and Ser. No. 697,387 which are incorporated herein by reference as if fully set forth.

The substituted 1,5-diazacycloalkane and 2-keto-1,5-diaza cycloalkane stabilizers, and the other compounding ingredients if used, can be admixed with substrates using known mixing techniques and equipment such as internal mixing kettles, a Banbury mixer, a Henschel mixer, a two-roll mill, an extruder mixer, or other standard equipment, to yield a composition which may be extruded, pressed, blowmolded or the like into film, fiber or shaped articles. Standard mixing times and temperatures can be employed. The objective is to obtain intimate and uniform mixing of the components. A favorable mixing procedure to use when adding the 2-keto-diazaalkane compound to a plastic material is to either dissolve or suspend the compound in a liquid such as hexane or benzene, add the plastic material in the form of a powder to the solution or suspension, evaporate off the liquid, and extruder mix the stabilized plastic material prior to forming the product.

The UV stability of a particular composition containing a polymeric material and a substituted 2-keto diazacycloalkane can be evaluated by exposing a prepared sample of the composition to Xenon or Carbon Arc light in a Weather-Ometer operating at a temperature, for example, of about 140° F. (60° C.). Degradation of the sample can be followed by periodically measuring the carbonyl absorption band at 1720 cm$^{-1}$ using an IR Spectrophotometer. The rapid formation of carbonyl indicates failure of the sample. This test procedure is well known, and is published in the text *Photodegradation, Photo-oxidation and Photostabilization of Polymers* by Ranby and Rabek, John Wiley and Sons, N.Y., N.Y., (1975) at page 129 et seq., and is disclosed in U.S. Pat. No. 3,909,493. Failure of the sample is also checked by visual signs of cracking when the sample is bent 180°.

Samples of the compositions can also be checked for oxidative and thermal stability by measuring the time to discoloration and/or embrittlement of the sample after aging in an air circulating oven at 140° C.

EXAMPLES

The following examples are given to further illustrate the invention. Detailed procedures are set forth for the preparation of compounds and compositions of this invention.

EXAMPLE 1

A. Preparation of 4,4-dimethyl-1,5-benzodiazepin-2-one by method described in Uzb.Khim.Zh. 1975, 19(2), 53–55 (Russ.) by Khakimova et al:

54 g o-phenylene diamine was dissolved in 50 ml toluene and 54 g 3,3-dimethylacrylic acid was added in a 500 ml 3-neck flask equipped with a magnetic stirrer, thermometer and a Dean-Stark trap. The mixture was heated at 125°–135° C. under argon until water started to form. 1.8 ml water was collected after 2.5 hr, and 7.3 ml water was collected after 2.2 hr. The reaction mixture is then cooled down and filtered. The solid is washed with benzene. 63.5 g of slightly brownish needles are secured.

B. Preparation of 4,4-dimethyl-decahydro-1,5-benzodiazepin-2-one by hydrogenation of compound obtained in Part A hereinabove.

11.8 g of the brownish needles obtained from the procedure of Part A hereinabove are mixed with 60 ml ethanol and 1 g Raney's Nickel washed twice with ethanol. The mixture was hydrogenated at 200° C. and 2000 psi for 3 hr. The reaction product is filtered and the solvent removed. The oil obtained solidified upon standing. Recrystallization from hexane yielded 10 g of a white solid.

The structure of the compound is confirmed by IR, NMR and mass spectro-meter data.

EXAMPLE 2

Preparation of trans-4,4-dimethyl-decahydro-1,5-benzodiazepin-2-one:

10.8 g β,β-dimethylacrylic acid was placed in a 250 ml flask, and 10 ml toluene was added followed by 11.4 g 1,2-diaminocyclohexane. The mixture is heated under an inert gas atmosphere, preferably argon, at 175°–180° C. with a Dean-Stark trap. 1.6 ml water was collected. The mixture is cooled down after 7 hr. Toluene was removed under vacuum. The reaction product obtained is recrystallized from acetone to give 2 g of a white crystalline product having a m.pt. of 188°–189° C.

Elemental analysis calculated: 14.27% N; 67.31% C; 10.7% H. Analysis found: 14.54% N; 68.22% C; 10.43% H.

The structure of the compound is supported by IR, NMR and mass spectrometer data.

EXAMPLE 3

Preparation of cis-$N^1$-ethyl-4,4-dimethyl-decahydro-1,5-benzodiazepin-2-one:

1.25 g sodium hydride (50% in oil) was dissolved in p-dioxane in a 250 ml flask, and 4.15 g cis-4,4-dimethyl-decahydro-1,5-benzodiazepin-2-one added. The mixture is stirred for about 1.5 hr. and cooled. 5.0 g ethyl iodide dissolved in 5 ml dioxane was added and the mixture stirred at 55°-60° C. overnight. It is then cooled and the solvent is removed to yield 4.67 g of an oily product. The structure of the compound obtained is confirmed by IR, NMR and mass spectrometer data.

In a manner analogous to that described hereinabove in this Example other alkyl derivatives may be substituted at the $N^1$ position.

EXAMPLE 4

Preparation of cis-$N^1$-dodecyl-4,4-dimethyl-decahydro-1,5-benzodiazepin-2-one:

1.25 g sodium hydride (50% in oil) was placed in a 250 ml flask, and 10 ml toluene (dried over molecular sieves) was added. After stirring 1 min under $N_2$ the solvent is removed with a pipette. Then 30 ml dry toluene are added followed by 4.15 g of cis-4,4-dimethyl-decahydro-1,5-benzodiazepin-2-one. After all the amide is dissolved, the mixture was refluxed and 5.73 g of 1-bromododecane in 10 ml toluene was added dropwise under nitrogen, over a period of about 30 min. The recation appeared to be complete after about 4 hrs. It was refluxed for an additional hour and cooled down. The reaction mixture is then poured into 100 ml water and extracted with benzene. The benzene solution was dried, filtered and concentrated. The oil was chromatographed on silica gel. 3.1 g of pure product are obtained.

EXAMPLE 5

Preparation of cis-$N^1$-benzyl-4,4-dimethyl-decahydro-1,5-benzodiazepin-2-one:

A. 1.1 g sodium hydride (50% in oil) was placed in a 100 ml flask, under argon. 20 ml toluene was added followed by 4.0 g cis-4,4-dimethyl-decahydro-1,5-benzodiazepin-2-one. The mixture was warmed to 90° C. and 5.5 g benzyl chloride in 10 ml toluene is added dropwise. The mixture was refluxed under argon overnight, then cooled and poured into 100 ml water. It is extracted with two aliquots of benzene, 100 ml each, which are dried over $Na_2SO_4$ and concentrated. A dark residue is obtained which is triturated with 20 ml pentane to yield 8.3 g of a gray solid. Upon recrystallization from ethanol with hydrazine hydrate, the color is removed and 15.1 g of a white solid are obtained.

B. trans-$N^1$-dodecyl-4,4-dimethyl-decahydro-1,5-benzodiazepin-2-one is prepared in a manner analogous to that in Ex. 5A above.

EXAMPLE 6

Preparation of 4,4,6,6-tetramethyl-1,5-diazepin-2-one:

4.4 g 2-methyl-1,2-propanediamine, 6.0 g 3,3-dimethylacrylic acid and 8 ml toluene were mixed and heated at 140°-150° C. overnight. The mixture was cooled and poured into 80 ml of 5% $Na_2CO_3$ solution; then extracted 3 times with 50 ml aliquots of chloroform. The combined chloroform solutions were dried and concentrated. Upon recrystallization from hexane-benzene a yellow crystalline solid, m. pt 129°-132° C., is obtained.

The structure of the compound is supported by IR, NMR and mass spectrometer data.

EXAMPLE 7

Preparation of $N^5$-($\beta$-hydroxyethyl)-4,4-dimethyl-decahydro-1,5-benzodiazepin-2-one:

38.6 g 4,4-dimethyl-decahydro-1,5-benzodiazepin-2-one is placed in a 250 ml flask with a slight molar excess of ethylene oxide (about 13.2 g) dissolved in ethyl alcohol. The reaction is run in an autoclave at 170°-180° C. A viscous brown paste is obtained which is dissolved in benzene. Upon recrystallization from benzene a white solid is obtained having a melting pt. 154°-156° C.

Elemental analysis calculated: 11.66% N; 64.97% C; 10.07% H. Analysis found 11.01% N; 65.0% C; 9.88% H.

The structure of the compound was confirmed by IR, NMR and mass spectrometer data.

The following Table I sets forth data obtained on tests conducted with 20 mil thickness samples of polypropylene. All samples contain 0.5 parts stabilizer per 100 parts resin (phr) and also include 0.25 phr of Irganox 1010 anti-oxidant.

TABLE I

| Example* | UV Stabilizer Additive | Xenon Weather-ometer Hours |
|---|---|---|
|  | None |  |
|  | Tinuvin ®327 2-(3',5'-di-t-butyl-2'-hydroxyphenyl)-5-chlorobenzotriazole | 1250 |
| 1B | cis-4,4-dimethyl-decahydro-1,5-benzodiazepin-2-one | 1400 |
| 6 | cis-$N^5$-($\beta$-hydroxyethyl)-4,4-dimethyl-decahydro-1,5-benzodiazepin-2-one | 3900 |
| as in 3 | cis-$N^1$-methyl-4,4-dimethyl-decahydro-1,5-benzodiazepin-2-one | ≅3500 |
| 5A | cis-$N^1$-benzyl-4,4-dimethyl-decahydro-1,5-benzodiazepin-2-one | ≅3500 |
| 5B | trans-$N^1$-dodecyl-4,4-dimethyl-decahydro-1,5-benzodiazepin-2-one | ≅7000 |
| 2 | trans-4,4-dimethyl-decahydro-1,5-benzodiazepin-2-one | ≅7000 |
| 4 | cis-$N^1$-dodecyl-4,4-dimethyl-decahydro-1,5-benzodiazepin-2-one | ≅3500 |
|  | Cyasorb ™ +531 | 6000 |

*Stabilizer prepared in a manner analogous to that described in the Example referred to, and set forth hereinbefore.
+available from American Cyanamid Co.

EXAMPLE 8

Preparation of 2,4,4-trimethyl-1,5-decahydrobenzodiazepine:

To a solution of 30 ml hexanes and 9.8 g mesityl oxide, 13.8 g potassium carbonate and 11.4 g 1,2-diaminocyclohexane were added. The mixture was stirred overnight under argon and refluxed for 70 hrs. Upon cooling the mixture was filtered, and the solvent removed. After distillation at 79°-83° C. under 9 mm hg, 10.5 g colorless oil is collected. The oil was dissolved in 100 ml ethanol and hydrogenated with 1 g Raney-Nickel at 100° C. and 1000 psi overnight. Upon cooling it was filtered and concentrated to yield a colorless oil. The oil was distilled and the fraction at 112°-8° C. under 9 mm Hg vacuum was collected.

The structure of the compound is supported by IR, NMR and mass spectrometer data.

EXAMPLE 9

Preparation of $N^1,N^5$-bis-$\beta$-hydroxyethyl-2,4,4-trimethyl-1,5-decahydrobenzodiazepine:

10 g of 2,4,4-trimethyl-1,5-decahydrobenzodiazepine, prepared as described in Example 8 hereinabove, and 8.8 g ethylene oxicle were mixed with 2 ml ethanol as catalyst and heated to 180° C. in an autoclave for 8.5 hrs. Cooled down and distilled the oil to collect yellow oil at 210°–220° C. 10.25 mm.

The following Table II sets forth data obtained on tests conducted with 10 mil thickness samples of polypropylene. All samples contain 0.5 parts stabilizer per 100 parts resin (phr) and also include 0.25 phr of Irganox 1010 antioxidant.

TABLE II

| Example* | UV Stabilizer Additive | Xenon Weather-ometer Hours |
|---|---|---|
|  | None | 400 |
|  | Tinuvin ®327 | 920 |
|  | Cyasorb TM +531 | 2920 |
| 1B | cis-4,4-dimethyl-decahydro-1,5-benzodiazepin-2-one | 1100 |
| 2 | trans-4,4-dimethyl-decahydro-1,5-benzodiazepin-2-one | 3200 |
| as in 3 | cis-$N^1$-methyl-4,4-dimethyl-decahydro-1,5-benzodiazepin-2-one | ≅2000 |
| 4 | cis-$N^1$-dodecyl-4,4-dimethyl-decahydro-1,5-benzodiazepin-2-one | ≅2000 |
| 5A | cis-$N^1$-benzyl-4,4-dimethyl-decahydro-1,5-benzodiazepin-2-one | 930 |
| 5B | trans-$N^1$-dodecyl-4,4-dimethyl-decahydro-1,5-benzodiazepin-2-one | ≅4000 |
| 6 | cis-$N^5$-($\beta$-hydroxyethyl)-4,4-dimethyl-decahydro-1,5-benzodiazepin-2-one | ≅2000 |

*Stabilizer prepared in a manner analogous to that described in the Example referred to, and set forth hereinbefore.
30available from American Cyanamid Co.

We claim:

1. A class of mono-keto compounds comprising polysubstituted monocyclic 2-keto-1,5-diazacycloalkanes having a fixed three-carbon bridge between the $N^1$ and $N^5$ atoms of the diaza ring, and dimers and bis compounds thereof containing plural 1,5-diazacycloalkan-2-one moieties, said mono-keto compounds having a formula selected from

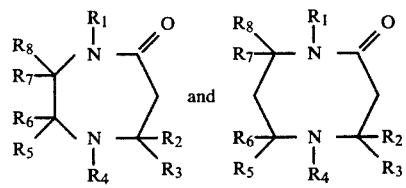

wherein,
said dimers and bis compounds consist essentially of two said moieties connected through N atoms thereof;
$R_1$ and $R_4$ independently represent hydrogen, alkyl having from 1 to about 24 carbon atoms, hydroxyalkyl having from 1 to about 12 carbon atoms, haloalkyl having from 1 to about 12 carbon atoms, cyanoalkyl having from 2 to about 12 carbon atoms, aminoalkyl or iminoalkyl having from 1 to about 12 carbon atoms, ether having from 3 to about 18 carbon atoms, hydroxyalkyl ether having from 4 to about 18 carbon atoms, cyanoalkyl ether having from 4 to about 18 carbon atoms, alkenyl having from 7 to about 14 carbon atoms, aralkyl having from 7 to about 14 carbon atoms, carboalkoxy having from 1 to 7 carbon atoms, and cycloalkyl having from 6 to about 7 carbon atoms;
$R_4$ optionally also represents oxygen;
$R_2$ and $R_3$ independently represent alkyl having from 1 to about 24 carbon atoms, haloalkyl having from 1 to about 12 carbon atoms, cyanoalkyl having from 2 to about 12 carbon atoms, cycloalkyl having from 5 to about 14 carbon atoms, hydroxycycloalkyl having from 5 to about 14 carbon atoms, aminoalkyl or iminoalkyl having from 2 to about 12 carbon atoms, alkenyl or aralkyl having from 7 to about 14 carbon atoms, carboalkoxy having from 1 to 7 carbon atoms, and cyclizable alkylene together having from 5 to about 6 carbon atoms which alkylene together with the carbon atom of the diaza ring to which said alkylene is bound represents cycloalkyl having from 6 to about 7 carbon atoms; and,
$R_5$, $R_6$, $R_7$, and $R_8$ independently represent hydrogen, alkyl having from 1 to about 24 carbon atoms, haloalkyl having from 1 to about 12 carbon atoms, cyanoalkyl having from 2 to about 12 carbon atoms, aminoalkyl or iminoalkyl having from 1 to about 12 carbon atoms, alkenyl or aralkyl having from 7 to about 14 carbon atoms, and cyclizable alkylene, $R_5$, $R_6$ together, or $R_7$, $R_8$ together, having from 5 to about 6 carbon atoms which alkylene together with the carbon atom of the diaza ring to which said alkylene is bound represents cycloalkyl having from 6 to about 7 carbon atoms.

2. The 2-keto-1,5-diazacycloalkanes of claim 1 wherein $R_1$ or $R_4$ or each is alkyl having from 1 to about 20 carbon atoms, and, $R_2$, $R_3$, $R_7$, and $R_8$, are each lower alkyl having from 1 to about 5 carbon atoms.

3. The 2-keto-1,5-diazacycloalkanes of claim 1 wherein $R_1$ or $R_4$ or each is alkyl having from 1 to about 20 carbon atoms, $R_2$, $R_3$, $R_5$ and $R_6$ are each lower alkyl having from 1 to about 5 carbon atoms.

4. The 2-keto-1,5-diazacycloalkanes of claim 1 selected from the group consisting of cis-4,4-dimethyl-decahydro-1,5-benzodiazepin-2-one;
trans-4,4-dimethyl-decahydro-1,5-benzodiazepin-2-one;
cis-$N^1$-methyl-4,4-dimethyl-decahydro-1,5-benzodiazepin-2-one;
cis-$N^1$-dodecyl-4,4-dimethyl-decahydro-1,5-benzodiazepin-2-one;
cis-$N^1$-benzyl-4,4-dimethyl-decahydro-1,5-benzodiazepin-2-one;
trans-$N^1$-dodecyl-4,4-dimethyl-decahydro-1,5-benzodiazepin-2-one; and,
cis-$N^5$-($\beta$-hydroxyethyl)-4,4-dimethyl-decahydro-1,5-benzodiazepin-2-one.

5. A composition of matter resistant to degradation by ultraviolet light comprising a compound subject to ultraviolet light degradation having dispersed therein from about 0.01 part to about 5 parts by weight of a polysubstituted monocyclic 2-keto-1,5-diazacycloalkane stabilizer compound, per 100 parts of said compound, said stabilizer compound being represented by a structure selected from the group consisting of

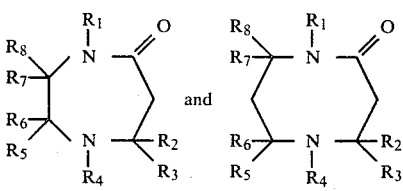

wherein, $R_1$ and $R_4$ independently represent hydrogen, alkyl having from 1 to about 24 carbon atoms, hydroxyalkyl having from 1 to about 12 carbon atoms, haloalkyl having from 1 to about 12 carbon atoms, cyanoalkyl having from 2 to about 12 carbon atoms, aminoalkyl or iminoalkyl having from 1 to about 12 carbon atoms, ether having from 3 to about 18 carbon atoms, hydroxyalkyl ether having from 4 to about 18 carbon atoms, cyanoalkyl ether having from 4 to about 18 carbon atoms, alkenyl having from 7 to about 14 carbon atoms, aralkyl having from 7 to about 14 carbon atoms, carboalkoxy having from 1 to 7 carbon atoms, and cycloalkyl having from 6 to about 7 carbon atoms;

$R_4$ optionally also represents oxygen; and, $R_2$ and $R_3$ independently represent alkyl having from 1 to about 24 carbon atoms, haloalkyl having from 1 to about 12 carbon atoms, cyanoalkyl having from 2 to about 12 carbon atoms, cycloalkyl having from 5 to about 14 carbon atoms, hydroxycycloalkyl having from 5 to about 14 carbon atoms, aminoalkyl or iminoalkyl having from 2 to about 12 carbon atoms, alkenyl or aralkyl having from 7 to about 14 carbon atoms, carboalkoxy having from 1 to 7 carbon atoms, and cyclizable alkylene together having from 5 to about 6 carbon atoms which alkylene together with the carbon atom of the diaza ring to which said alkylene is bound represents cycloalkyl having from 6 to about 7 carbon atoms.

6. The composition of claim 5 wherein said compound is selected from the group consisting of polyhydrocarbons, polyesters, polyester resin, polyamides, vinyl polymers, cellulose ether, and cellulose esters.

7. The composition of claim 6 wherein said compound is a solid and said 2-keto-1,5-diazacycloalkanes have a structure wherein $R_1$ or $R_4$ or each is alkyl having from 1 to about 20 carbon atoms, and, $R_2$, $R_3$, $R_7$, and $R_8$, are each lower alkyl having from 1 to about 5 carbon atoms.

8. The composition of claim 6 wherein said compound is a solid and said 2-keto-1,5-diazacycloalkanes have a structure wherein $R_1$ or $R_4$ or each is alkyl having from 1 to about 20 carbon atoms, $R_2$, $R_3$, $R_5$ and $R_6$ are each lower alkyl having from 1 to about 5 carbon atoms.

9. The composition of claim 6 wherein said compound is a solid and said 2-keto-1,5-diazacycloalkanes are selected from the group consisting of
cis-4,4-dimethyl-decahydro-1,5-benzodiazepin-2-one;
trans-4,4-dimethyl-decahydro-1,5-benzodiazepin-2-one;
cis-$N^1$-methyl-4,4-dimethyl-decahydro-1,5-benzodiazepin-2-one;
cis-$N^1$-dodecyl-4,4-dimethyl-decahydro-1,5-benzodiazepin-2-one;
cis-$N^1$-benzyl-4,4-dimethyl-decahydro-1,5-benzodiazepin-2-one;
trans-$N^1$-dodecyl-4,4-dimethyl-decahydro-1,5-benzodiazepin-2-one; and,
cis-$N^5$-($\beta$-hydroxyethyl)-4,4-dimethyl-decahydro-1,5-benzodiazepin-2-one.

10. A class of mono-keto compounds comprising polysubstituted bicyclic 2-keto-1,5-diazacycloalkanes having a fixed three-carbon bridge between the $N^1$ and $N^5$ atoms of the diaza ring, and dimers and bis compounds thereof containing plural 1,5-diazacycloalkan-2-one moieties, said mono-keto compounds having a formula selected from

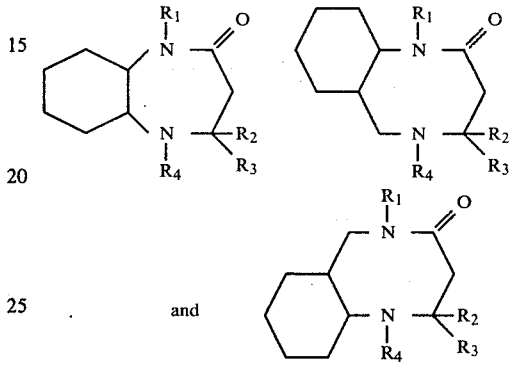

and wherein, said dimers and bis compounds consist essentially of two said moieties connected through N atoms thereof;

$R_1$ and $R_4$ independently represent hydrogen, alkyl having from 1 to about 24 carbon atoms, hydroxyalkyl having from 1 to about 12 carbon atoms, haloalkyl having from 1 to about 12 carbon atoms, cyanoalkyl having from 2 to about 12 carbon atoms, aminoalkyl or iminoalkyl having from 1 to about 12 carbon atoms, ether having from 3 to about 18 carbon atoms, hydroxyalkyl ether having from 4 to about 18 carbon atoms, cyanoalkyl ether having from 4 to about 18 carbon atoms, alkenyl having from 7 to about 14 carbon atoms, aralkyl having from 7 to about 14 carbon atoms, carboalkoxy having from 1 to 7 carbon atoms, and cycloalkyl having from 6 to about 7 carbon atoms;

$R_4$ optionally also represents oxygen;

$R_2$ and $R_3$ independently represent alkyl having from 1 to about 24 carbon atoms, haloalkyl having from 1 to about 12 carbon atoms, cyanoalkyl having from 2 to about 12 carbon atoms, cycloalkyl having from 5 to about 14 carbon atoms, hydroxycycloalkyl having from 5 to about 14 carbon atoms, aminoalkyl or iminoalkyl having from 2 to about 12 carbon atoms, alkenyl or aralkyl having from 7 to about 14 carbon atoms, carboalkoxy having from 1 to 7 carbon atoms, and cyclizable alkylene together having from 5 to about 6 carbon atoms which alkylene together with the carbon atom of the diaza ring to which said alkylene is bound represents cycloalkyl having from 6 to about 7 carbon atoms; and, $R_5$, $R_6$, $R_7$, and $R_8$ independently represent hydrogen, alkyl having from 1 to about 24 carbon atoms, haloalkyl having from 1 to about 12 carbon atoms, cyanoalkyl having from 2 to about 12 carbon atoms, aminoalkyl or iminoalkyl having from 1 to about 12 carbon atoms, alkenyl or aralkyl having from 7 to about 14 carbon atoms, and cyclizable alkylene, $R_5$, $R_6$ together, or $R_7$, $R_8$ together, having from 5 to about 6 carbon atoms which alkylene together with the carbon atom of the diaza ring to which said alkylene is bound represents cycloalkyl having from 6 to about 7 carbon atoms.

11. The 2-keto-1,5-diazacycloalkanes of claim 10 wherein $R_1$ or $R_4$ or each is alkyl having from 1 to about 20 carbon atoms, and, $R_2$, $R_3$, $R_7$, and $R_8$, are each lower alkyl having from 1 to about 5 carbon atoms.

12. The 2-keto-1,5-diazacycloalkanes of claim 10 wherein $R_1$ or $R_4$ or each is alkyl having from 1 to about 20 carbon atoms, $R_2$, $R_3$, $R_5$ and $R_6$ are each lower alkyl having from 1 to about 5 carbon atoms.

13. A composition of matter resistant to degradation by ultraviolet light comprising a compound subject to ultraviolet light degradation having dispersed therein from about 0.01 part to about 5 parts by weight of a bicyclic polysubstituted 2-keto-1,5-diazacycloalkane stabilizer compound, per 100 parts of said compound, said stabilizer compound being represented by a structure selected from the group consisting of

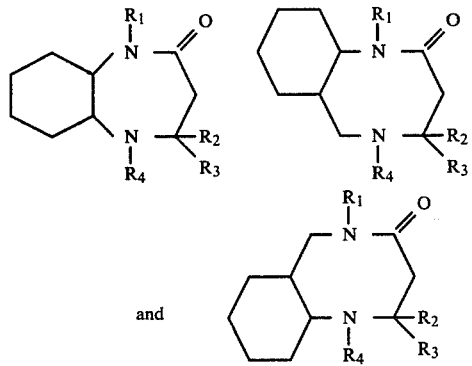

and wherein,
$R_1$ and $R_4$ independently represent hydrogen, alkyl having from 1 to about 24 carbon atoms, hydroxyalkyl having from 1 to about 12 carbon atoms, haloalkyl having from 1 to about 12 carbon atoms, cyanoalkyl having from 2 to about 12 carbon atoms, aminoalkyl or iminoalkyl having from 1 to about 12 carbon atoms, ether having from 3 to about 18 carbon atoms, hydroxyalkyl ether having from 4 to about 18 carbon atoms, cyanoalkyl ether having from 4 to about 18 carbon atoms, alkenyl having from 7 to about 14 carbon atoms, aralkyl having from 7 to about 14 carbon atoms, carboalkoxy having from 1 to 7 carbon atoms, and cycloalkyl having from 6 to about 7 carbon atoms;

$R_4$ optionally also represents oxygen; and, $R_2$ and $R_3$ independently represent alkyl having from 1 to about 24 carbon atoms, haloalkyl having from 1 to about 12 carbon atoms, cyanoalkyl having from 2 to about 12 carbon atoms, cycloalkyl having from 5 to about 14 carbon atoms, hydroxycycloalkyl having from 5 to about 14 carbon atoms, aminoalkyl or iminoalkyl having from 2 to about 12 carbon atoms, alkenyl or aralkyl having from 7 to about 14 carbon atoms, carboalkoxy having from 1 to 7 carbon atoms, and cyclizable alkylene together having from 5 to about 6 carbon atoms which alkylene together with the carbon atom of the diaza ring to which said alkylene is bound represents cycloalkyl having from 6 to about 7 carbon atoms.

14. The composition of claim 13 wherein said compound is selected from the group consisting of polyhydrocarbons, polyesters, polyester resins, polyamides, vinyl polymers, cellulose ether, and cellulose esters.

15. The composition of claim 14 wherein said compound is a solid and said 2-keto-1,5-diazacycloalkanes have a structure wherein $R_1$ or $R_4$ or each is alkyl having from 1 to about 20 carbon atoms, and, $R_2$, $R_3$, $R_7$, and $R_8$, are each lower alkyl having from 1 to about 5 carbon atoms.

16. The composition of claim 14 wherein said compound is a solid and said 2-keto-1,5-diazacycloalkanes have a structure wherein $R_1$ or $R_4$ or each is alkyl having from 1 to about 20 carbon atoms, $R_2$, $R_3$, $R_5$ and $R_6$ are each lower alkyl having from 1 to about 5 carbon atoms.

* * * * *